(12) United States Patent
Li et al.

(10) Patent No.: US 11,596,810 B2
(45) Date of Patent: Mar. 7, 2023

(54) IMAGE GUIDING DEVICE AND RADIOTHERAPY EQUIPMENT

(71) Applicant: OUR UNITED CORPORATION, Shaanxi (CN)

(72) Inventors: Jiuliang Li, Shaanxi (CN); Hao Yan, Shaanxi (CN); Renqing Liu, Shaanxi (CN); Ming Zhong, Shaanxi (CN); Jinsheng Li, Shaanxi (CN)

(73) Assignee: Our United Corporation, Shaanxi (CN)

( * ) Notice: Subject to any disclaimer, the term of this patent is extended or adjusted under 35 U.S.C. 154(b) by 147 days.

(21) Appl. No.: 16/979,126

(22) PCT Filed: Mar. 8, 2019

(86) PCT No.: PCT/CN2019/077450
§ 371 (c)(1),
(2) Date: Sep. 8, 2020

(87) PCT Pub. No.: WO2019/170137
PCT Pub. Date: Sep. 12, 2019

(65) Prior Publication Data
US 2020/0398081 A1    Dec. 24, 2020

(30) Foreign Application Priority Data

Mar. 8, 2018    (CN) .......................... 201810190464.1

(51) Int. Cl.
*A61N 5/10*    (2006.01)
(52) U.S. Cl.
CPC ......... *A61N 5/1049* (2013.01); *A61N 5/1081* (2013.01); *A61N 2005/1061* (2013.01)
(58) Field of Classification Search
CPC ........ A61N 5/10; A61N 5/103; A61N 5/1048; A61N 5/1049; A61N 5/1064;
(Continued)

(56) References Cited

U.S. PATENT DOCUMENTS

2004/0131144 A1* 7/2004 Nishide ................ A61B 6/032
378/19
2004/0247070 A1* 12/2004 Ali ........................ G06T 11/006
378/4

FOREIGN PATENT DOCUMENTS

CN    202397484 U    8/2012
CN    102698374 A    10/2012
(Continued)

OTHER PUBLICATIONS

International search report of PCT application No. PCT/CN2019/077450 dated May 23, 2019.
First office action of Chinese application No. 201810190464.1 dated Jun. 12, 2019.
Second office action of Chinese application No. 201810190464.1 dated Jan. 20, 2020.
(Continued)

*Primary Examiner* — Hoon K Song
(74) *Attorney, Agent, or Firm* — Knobbe, Martens, Olson & Bear, LLP (57) ABSTRACT

An image guiding device includes a gantry, an imaging source, an imager, and an image server. The imaging source, the imager and the image server are all mounted on the gantry. The imager is connected to the image server. The imaging source is arranged to face the imager. The imaging source emits X-rays. The imager receives X-rays passing through an affected part of a patient, generates projection data based on the received X-rays, and sends the projection data to the image server. The image server processes the projection data to obtain an image of the affected part.

19 Claims, 8 Drawing Sheets

(58) Field of Classification Search
CPC .. A61N 5/1071; A61N 5/1077; A61N 5/1081; A61N 2005/1061; A61N 2005/1074; A61N 2005/1092; A61B 6/04; A61B 6/0407; A61B 6/44; A61B 6/4429; A61B 6/4435; A61B 6/46; A61B 6/461; A61B 6/462; A61B 6/52; A61B 6/54; A61B 6/542; A61B 6/548; A61B 6/56; A61B 6/563; A61B 34/25; A61B 2560/02; A61B 2560/0204; A61B 2560/0214; A61B 2560/04; A61B 2560/0443; A61B 2560/045; A61B 2560/0487; G06T 1/00; G06T 1/0007; G06T 11/003; G06T 2200/28

See application file for complete search history.

(56) References Cited

FOREIGN PATENT DOCUMENTS

| | | |
|---|---|---|
| CN | 108186039 A | 6/2018 |
| CN | 208464101 U | 2/2019 |
| JP | H05123316 A | 5/1993 |
| WO | 2014005049 A1 | 1/2014 |
| WO | WO-2014005049 A1 * | 1/2014 ............. A61B 6/032 |

OTHER PUBLICATIONS

Rejection Decision of Chinese application No. 201810190464.1 dated May 28, 2020.

* cited by examiner

IMAGE GUIDING DEVICE AND RADIOTHERAPY EQUIPMENT

CROSS-REFERENCE TO RELATED APPLICATIONS

The present disclosure is a national phase application based on PCT/CN2019/077450, filed on Mar. 18, 2019, claims priority to Chinese Patent Application No. 201810190464.1, filed on Mar. 8, 2018 and entitled "IMAGE GUIDING DEVICE AND RADIOTHERAPY EQUIPMENT", the contents of which are incorporated herein by reference in their entireties.

TECHNICAL FIELD

The present disclosure relates to the technical field of medical instruments, and in particular relate to an image guiding device and a radiotherapy equipment.

BACKGROUND

Radiotherapy is the treatment of tumors by using radioactive rays to realize death or apoptosis of cancer cells, and is one of the most basic and important methods for the treatment of tumors. As tumor tissues are surrounded by healthy tissues, the tumor tissues need to be precisely positioned during the radiotherapy, so as to avoid damages to the healthy tissues. The positioning of the tumor tissues may be achieved by an image guiding device. The image guiding device may be configured to collect image information of the human body, determine the position and movement of a treatment target area based on the image information, and guide the subsequent treatment.

SUMMARY

Embodiments of the present disclosure provide an image guiding device and a radiotherapy equipment. The technical solutions are summarized as follows.

In an aspect, an image guiding device is provided. The image guiding device includes: a gantry; an imaging source mounted on the gantry and configured to emit X-rays; an imager arranged on the gantry in a fashion of facing the imaging source at 180 degrees, and configured to receive the X-rays passing through an affected part of a patient and generate projection data according to the received X-rays; and an image server mounted on the gantry, connected to the imager and configured to receive the projection data and process the projection data to obtain an image of the affected part; wherein when the gantry rotates, the imager and the image server are in a stationary state relative to each other.

Optionally, the image server includes an image reconstruction unit and an image registration unit; or the image server includes an image reconstruction server with an image reconstruction unit, and an image registration server with an image registration unit, wherein the image reconstruction server is in communication with the image registration server; or the image server includes an image reconstruction unit and the image guiding device further includes an image registration server with an image registration unit, wherein the image server is in communication with the image registration server, and the image registration server is arranged separately from the gantry;

wherein the image reconstruction unit is configured to reconstruct the projection data to obtain a first image, and send the first image to the image registration unit; and the image registration unit is configured to register the first image to obtain a second image.

Optionally, the image guiding device further includes a control server arranged separately from the gantry; wherein
when the image server includes the image reconstruction unit and the image registration unit, the control server is in communication with the image server; and
when the image server includes the image reconstruction server and the image registration server or when the image registration server is arranged separately from the gantry, the control server is in communication with the image registration server.

Optionally, when the image registration server is arranged separately from the gantry, the control server and the image registration server are integrated in one physical machine.

Optionally, the image guiding device further includes an image display arranged separately from the gantry; wherein
when the image server includes the image reconstruction unit and the image registration unit or when the image server includes the image reconstruction server and the image registration server, the image display is in communication with the control server; and
when the image registration server is arranged separately from the gantry, the image display is in communication with the image registration server.

Optionally, the image guiding device further includes an exposure controller and a high voltage generator; wherein
the exposure controller and the high voltage generator are mounted on the gantry, the exposure controller is respectively connected to the high voltage generator and the image server, and the high voltage generator is connected to the imaging source;
wherein the image server is configured to send a scanning instruction message to the exposure controller; and the exposure controller is configured to control the imaging source to emit the X-rays by the high voltage generator and control the imager to receive the X-rays according to the scanning instruction message.

Optionally, the image guiding device further includes a treatment couch;
wherein the treatment couch is mounted in an accommodation chamber of the gantry.

Optionally, the gantry is rotatable around a rotation center thereof at any angle within 360 degrees.

Optionally, the imaging source is a bulb tube, and the imager is a flat panel detector.

In another aspect, a radiotherapy equipment is provided. The radiotherapy equipment includes the above-mentioned image guiding device.

BRIEF DESCRIPTION OF DRAWINGS

In order to describe the technical solutions in the embodiments of the present disclosure more clearly, the following briefly introduces the accompanying drawings required for describing the embodiments. Apparently, the accompanying drawings in the following description show merely some embodiments of the present disclosure, and persons of ordinary skilled in the art may also derive other drawings from these accompanying drawings without creative efforts.

Reference numerals and denotations thereof:
1—gantry; a—rotation center of the gantry; A—accommodation chamber of the gantry; 2—imaging source; 3—imager; 4—image server; 5—treatment couch; 6—exposure controller; 7—high voltage generator; 81—image reconstruction unit; 82—image registration unit; 91—image reconstruction server; 92—image registration server; 10—control server; 11—image display.

DESCRIPTION OF EMBODIMENTS

For clearer descriptions of the objects, technical solutions, and advantages of the present disclosure, the embodiments of the present disclosure are described in detail in combination with the accompanying drawings.

Figure 1:
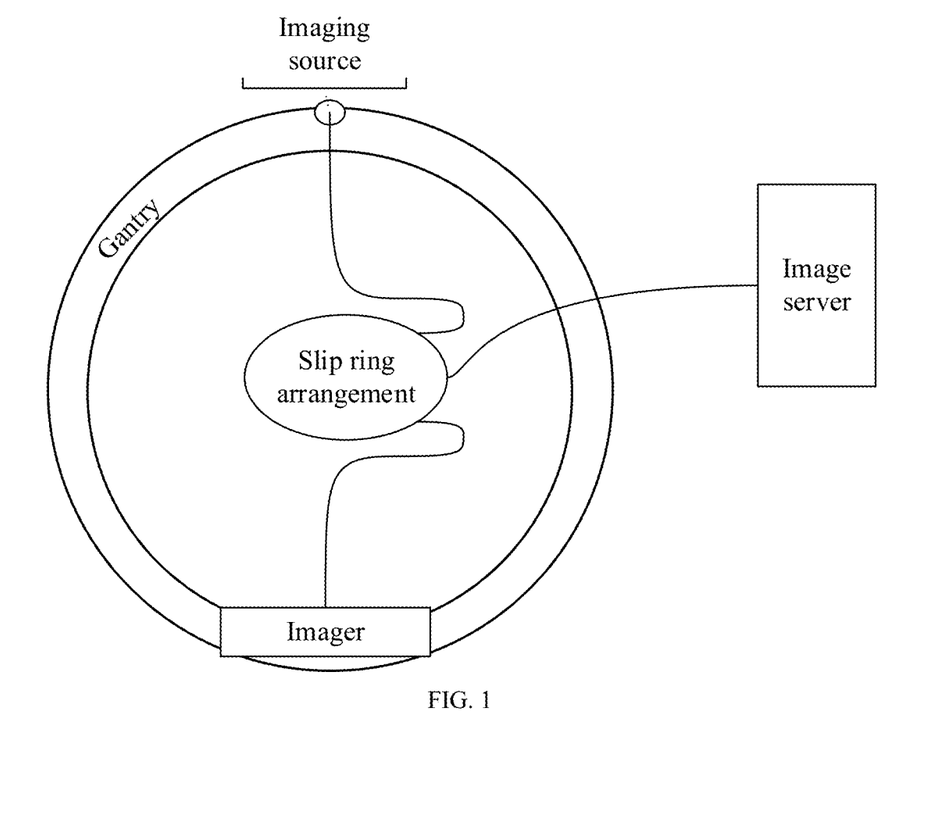
FIG. 1 is a schematic structural diagram of an image guiding device according to the related art.

At present, as shown in FIG. 1, the image guiding device generally includes a gantry, an imaging source, an imager, a slip ring arrangement, and an image server. The imaging source and the imager are mounted on the gantry. The imaging source, the imager, and the image server are connected to the slip ring arrangement respectively. When the image guiding device is in use, the slip ring arrangement supplies high-voltage power to the imaging source, such that X-rays emitted by the imaging source can pass through an affected part of a patient. Meanwhile, the slip ring arrangement sends a pulse signal to the imager to instruct the imager to synchronously receive the X-rays passing through the affected part of the patient. The imager generates projection data according to the received X-rays, and transmits the projection data to the image server by the slip ring arrangement. The image server reconstructs and registers the projection data to obtain an image of the affected part.

However, since the imager is indirectly connected to the image server by the slip ring set, a rate of data transmission between the imager and the image server is relatively low. In this way, the projection data transmitted by the imager to the image server is easy to lose, resulting in low accuracy of the image of the affected part obtained by the image server according to the projection data, thereby affecting subsequent positioning and image guiding effects. In addition, since the slip ring arrangement is relatively high in cost and susceptible to damages after long-term use, and needs to be replaced frequently, the manufacturing cost and the maintenance cost of the image guiding device are relatively high.

Figure 2:
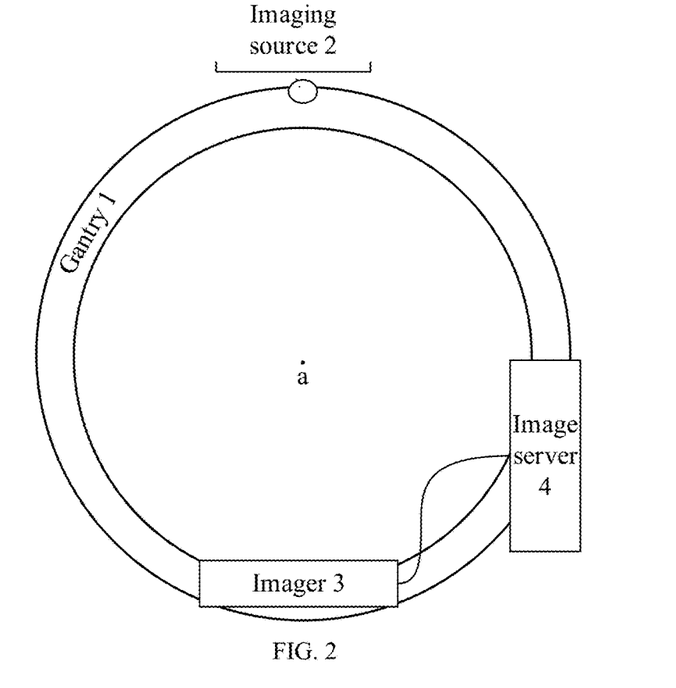
FIG. 2 is a schematic structural diagram of a first image guiding device according to an embodiment of the present disclosure.

FIG. 2 is a schematic structural diagram of an image guiding device according to an embodiment of the present disclosure. Referring to FIG. 2, the image guiding device may include a gantry 1, an imaging source 2, an imager 3, and an image server 4.

The imaging source 2, the imager 3, and the image server 4 are all mounted on the gantry 1. The imager 3 is connected to the image server 4.

It should be noted that the gantry 1 may be a drum-type gantry. In practice, the gantry 1 is rotatable around a rotation center a thereof at any angle within 360 degrees.

In addition, the imaging source 2 is configured to emit X-rays. For example, the imaging source 2 may be a bulb tube, or the like. The imager 3 is configured to receive the X-rays. For example, the imager 3 may be a flat panel detector, or the like. The imaging source 2 is arranged in a fashion of facing the imager 3 at 180 degrees, that is, a virtual connecting line between the imaging source 2 and the imager 3 passes through the rotation center a of the gantry 1.

Furthermore, the imager 3 may be connected to the image server 4 via a high-speed network cable or the like, which is not limited in the embodiment of the present disclosure.

When the image guiding device is in use, the imaging source 2 may emit X-rays. The imager 3 may receive the X-rays passing through an affected part of a patient, generate projection data according to the received X-rays, and send the projection data to the image server 4. Afterwards, the image server 4 may process the projection data to obtain an image of the affected part.

It should be noted that, since both the imaging source 2 and the imager 3 are mounted on the gantry 1, when the gantry 1 rotates, the imaging source 2 and the imager 3 may rotate at the same time. In this way, during the process of emitting the X-rays by the imaging source 2 and receiving the X-rays by the imager 3, the imager 3 is capable of acquiring a projection of the X-rays passing through the affected part of the patient to obtain projection data, thereby realizing the scanning of the affected part of the patient.

It is worth noting that, since both the imager 3 and the image server 4 are mounted on the gantry 1, when the gantry 1 rotates, the imager 3 and the image server 4 are in a stationary state relative to each other. As the imager 3 is directly connected to the image server 4, a rate of data transmission between the imager 3 and the image server 4 is relatively high, and the imager 3 may send the projection data to the image server 4 completely and accurately. In this way, the image of the affected part obtained by the image server 4 based on the projection data is more accurate and the image quality is higher, thereby improving the subsequent positioning and image guiding effects.

In addition, compared to the structure in the related art that only the imaging source and the imager are mounted on the gantry, and the imaging source and the imager are indirectly connected to other components outside the gantry by a slip ring arrangement, the image guiding device according to the embodiment of the present disclosure omits the slip ring arrangement, in this way, the imaging quality can be improved, and the manufacturing cost and the maintenance cost of the image guiding device can be greatly reduced.

Figure 3:
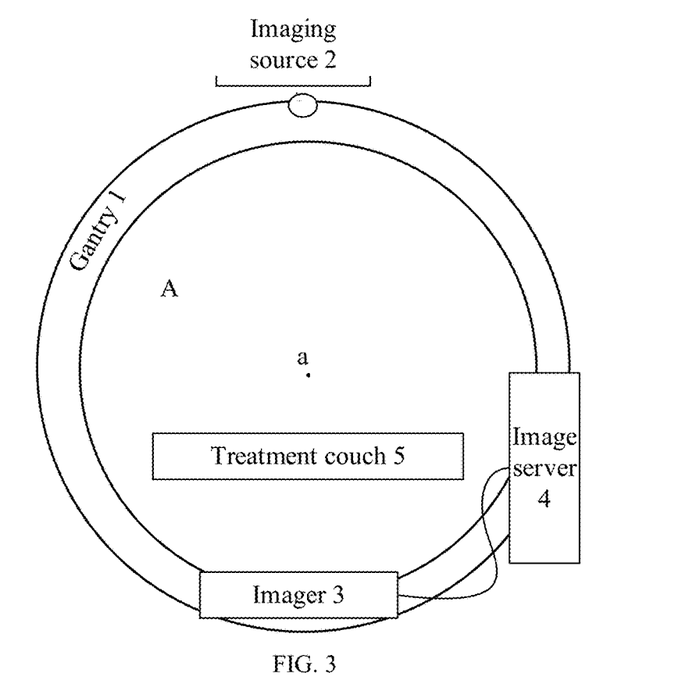
FIG. 3 is a schematic structural diagram of a second image guiding device according to an embodiment of the present disclosure.

Further, referring to FIG. 3, the image guiding device may further include a treatment couch 5.

The treatment couch 5 is mounted in an accommodation chamber A of the gantry 1.

It should be noted that the accommodation chamber A for accommodating the patient may be provided in the gantry 1. The treatment couch 5 for supporting the patient may be arranged at the accommodation chamber A. In practice, the patient may lie on the treatment couch 5, and the affected part of the patient can be scanned by a rotating beam of the X-rays formed by rotating movements of the imaging source 2 and the imager 3 on the gantry 1, in conjunction with a translational or rotational movement of the treatment couch 5.

Figure 4:
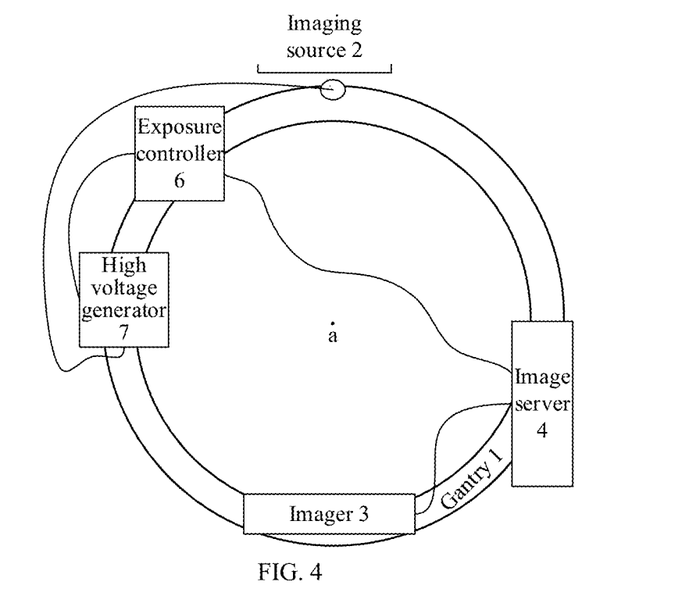
FIG. 4 is a schematic structural diagram of a third image guiding device according to an embodiment of the present disclosure.

Further, referring to FIG. 4, the image guiding device may further include an exposure controller 6 and a high voltage generator 7.

The exposure controller 6 and the high voltage generator 7 are mounted on the gantry 1. The exposure controller 6 is connected to the high voltage generator 7 and the image server 4 respectively. The high voltage generator 7 is connected to the imaging source 2.

It should be noted that the exposure controller 6 is configured to control the emission and reception of the X-rays, and the high voltage generator 7 is a high-voltage power supply that can supply high-voltage power in a kilovolt level.

In addition, the exposure controller 6 may be connected to the high-voltage generator 7 and the image server 4 respectively by serial port lines and the like. The high voltage generator 7 may be connected to the imaging source 2 by a high-voltage line or the like, which is not limited in the embodiment of the present disclosure.

When the image guiding device is in use, the image server 4 may send a scanning instruction message to the exposure controller 6. When receiving the scanning instruction message, the exposure controller 6 may control the imaging source 2 to emit X-rays by the high voltage generator 7 and control the imager 3 to receive the X-rays according to the scanning instruction message.

It should be noted that the scanning instruction message is used to instruct to scan the affected part of the patient. In addition, the scanning instruction message may be actively generated by the image server 4, or may be generated by other control components included in the image guiding device and then sent to the image server 4, which is not limited in the embodiment of the present disclosure.

In addition, the exposure controller 6 may control the high voltage generator 7 to supply high-voltage power to the imaging source 2 when controlling the imaging source 2 to emit the X-rays by the high voltage generator 7, such that the imaging source 2 generates and emits the X-rays. The exposure controller 6 may send a pulse signal to the imager 3 by a device such as a pulse signal generator when controlling the imager 3 to receive the X-rays, so as to instruct the imager 3 to receive the X-rays synchronously.

It is worth noting that, in the embodiment of the present disclosure, these image acquisition components, such as the imaging source 2, the imager 3, the image server 4, the exposure controller 6 and the high-voltage generator 7, which impose relatively high requirements on data processing, are all mounted on the gantry 1, such that these image acquisition components may be in a stationary state relative to each other when the gantry 1 rotates. In this way, the image server 4 may quickly instruct the imaging source 2 and the imager 3 to perform scanning by the exposure controller 6, and the imager 3 may also quickly send projection data obtained by scanning to the image server 4, thereby improving the image acquisition efficiency.

Figure 5:
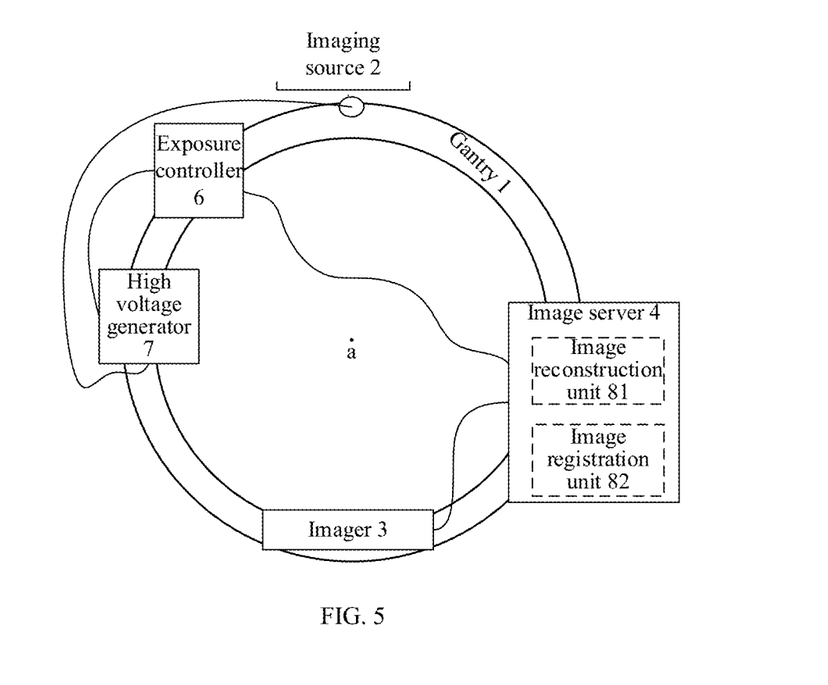
FIG. 5 is a schematic structural diagram of a fourth image guiding device according to an embodiment of the present disclosure.
Figure 6:
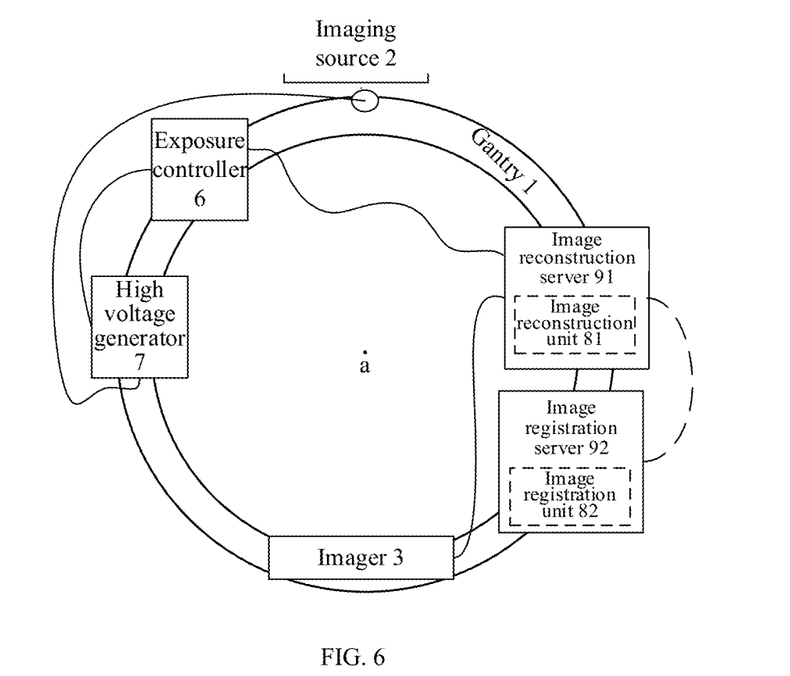
FIG. 6 is a schematic structural diagram of a fifth image guiding device according to an embodiment of the present disclosure.
Figure 7:
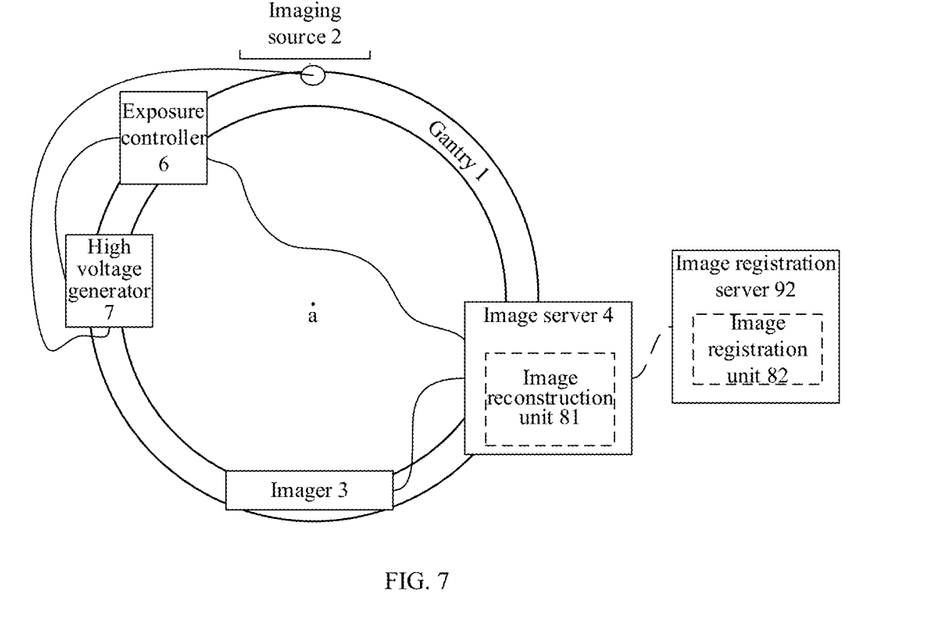
FIG. 7 is a schematic structural diagram of a sixth image guiding device according to an embodiment of the present disclosure.

Further, referring to FIG. 5, FIG. 6 or FIG. 7, the image guiding device may include an image reconstruction unit 81 and an image registration unit 82.

Referring to FIG. 5, the image server 4 includes an image reconstruction unit 81 and an image registration unit 82.

Optionally, referring to FIG. 6, the image server 4 includes an image reconstruction server 91 with an image reconstruction unit 81 and an image registration server 92 with an image registration unit 82, wherein the image reconstruction server 91 is in communication with the image registration server 92.

Optionally, referring to FIG. 7, the image server 4 includes an image reconstruction unit 81 and the image guiding device further includes an image registration server 92 with an image registration unit 82, wherein the image server 4 is in communication with the image registration server 92 and the image registration server 92 is arranged separately from the gantry 1.

It should be noted that, when the image reconstruction server 91 is in communication with the image registration server 92, or when the image server 4 is in communication with the image registration server 92, both the communicative connections can be established over a wired network (such as Ethernet) or a wireless network (such as wireless fidelity (Wi-Fi) network).

In addition, in FIG. 5, the image reconstruction unit 81 and the image registration unit 82 are both arranged in the image server 4, that is, they are integrated in one physical machine, thereby reducing the number of hardware to be deployed. In FIG. 6, the image reconstruction unit 81 is arranged in the image reconstruction server 91, the image registration unit 82 is arranged in the image registration server 92, and the image reconstruction server 91 and the image registration server 92 constitute the image server 4. In the case, the image reconstruction unit 81 and the image registration unit 82 are separately arranged in different physical machines, thereby making deployment more flexible. In FIG. 7, the image reconstruction unit 81 is arranged in the image server 4, the image registration unit 82 is arranged in the image registration server 92, and the image registration server 92 is arranged separately from the gantry. For example, when the gantry 1 is arranged in a machine room for radiotherapy, the image registration server 92 can be arranged in a control room, and the image registration server 92 may be in communication with the image server 4 in this case over a Wi-Fi network.

When the image guiding device is in use, the image reconstruction unit 81 may reconstruct the projection data to obtain a first image, wherein the first image may be a three-dimensional image. Then, the image reconstruction unit 81 may send the first image to the image registration unit 82. The image registration unit 82 may register the first image to obtain a second image while receiving the first image, wherein the second image may be a guiding image for guiding a subsequent treatment. Both the first image and the second image are images of the affected part.

It should be noted that, when the image registration unit 82 registers the first image to obtain the second image, registration information of the first image may be obtained by comparing the first image with a preset radiotherapy planning image, and then the second image is obtained by adjusting the first image according to the registration information.

In addition, the radiotherapy planning image may be set in advance. For example, the radiotherapy planning image may be an image obtained by other medical imaging device, such as a computed tomography (CT) simulator, according to a patient's radiotherapy plan generated by treatment planning system (TPS).

Moreover, the registration information of the first image is configured to instruct a body position deviation of the patient. For example, the registration information of the first image may include information such as an orientation inclination and a position deflection of the first image relative to the radiotherapy planning image.

Further, referring to FIG. 8, FIG. 9, FIG. 10, or FIG. 11, the image guiding device may further include a control server 10, which is arranged separately from the gantry 1.

Figure 8:
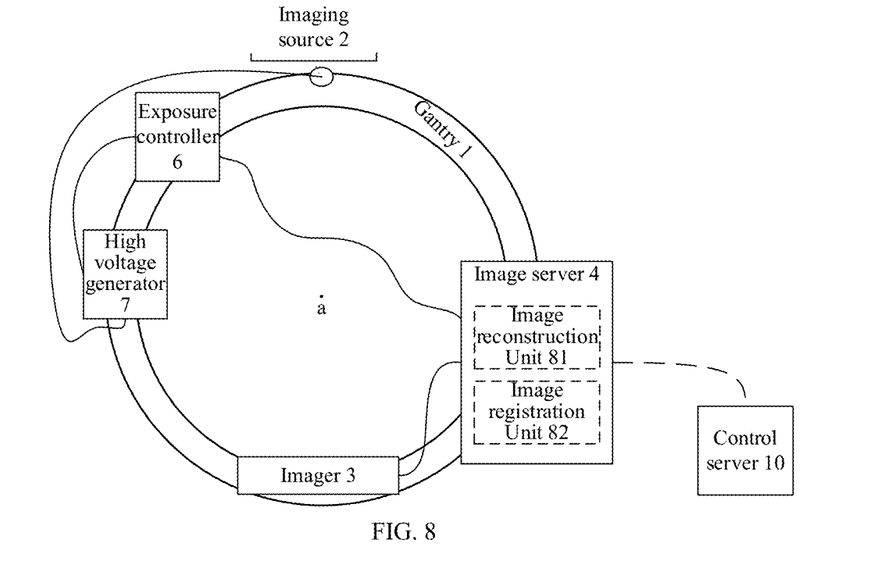
FIG. 8 is a schematic structural diagram of a seventh image guiding device according to an embodiment of the present disclosure.
Figure 9:
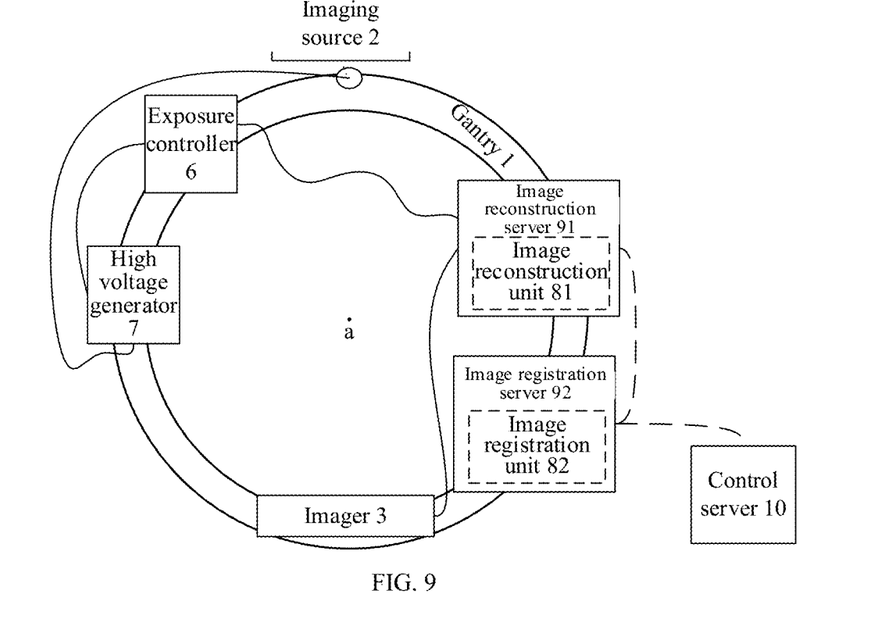
FIG. 9 is a schematic structural diagram of an eighth image guiding device according to an embodiment of the present disclosure.
Figure 10:
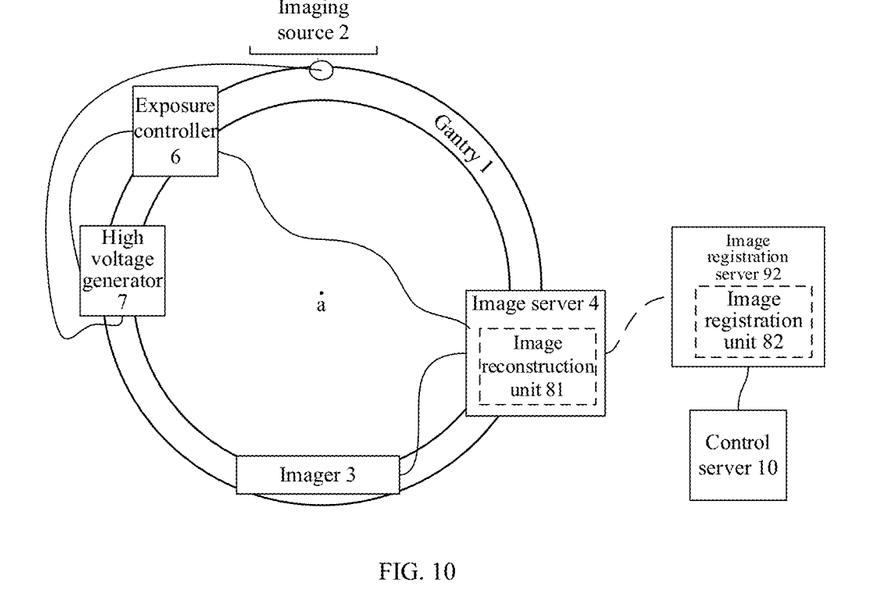
FIG. 10 is a schematic structural diagram of a ninth image guiding device according to an embodiment of the present disclosure.
Figure 11:
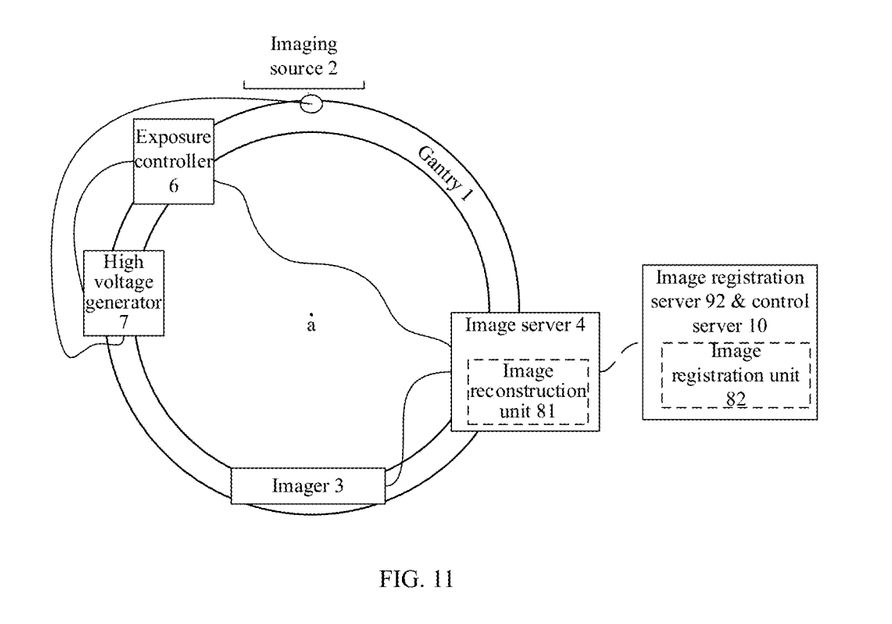
FIG. 11 is a schematic structural diagram of a tenth image guiding device according to an embodiment of the present disclosure.

Referring to FIG. 8, when the image server 4 includes the image reconstruction unit 81 and the image registration unit 82, the control server 10 is in communication with the image server 4. Referring to FIG. 9, FIG. 10 or FIG. 11, when the image server 4 includes the image reconstruction server 91 and the image registration server 92, or when the image registration server 92 is arranged separately from the gantry 1, the control server 10 is in communication with the image registration server 92.

It should be noted that, when the control server 10 is in communication with the image server 4, or when the control server 10 is in communication with the image registration server 92, the communication connection may be established over a wired network or a wireless network.

In addition, when the control server 10 is in communication with the image server 4, or when the control server 10 is in communication with the image registration server 92, the control server 10 may control an image processing operation of the image server 4 or the image registration server 92. For example, when the control server 10 is in communication with the image server 4, control software may be installed in the control server 10 and image software may be installed in the image server 4, the control server 10 may start the image software in the image server 4 in a remote desktop fashion by the control software, so as to start collecting images.

It should be noted that the image registration unit 82 may send the registration information of the first image to the control server 10, and the control server 10 may perform position control operations according to the registration information while receiving the registration information.

In addition, the control server 10 may control the rotation of the gantry 1, the movement of the treatment couch 5, the position of the imaging source 2, the position of the imager 3 and the like according to the registration information while performing the position control operations according to the registration information, such that the body position of the patient can be adjusted according to these position control operations, thereby reducing positioning errors to facilitate accurately performing the subsequent radiotherapy.

It is worth noting that, when the image registration server 92 is arranged separately from the gantry 1, referring to FIG. 10, the control server 10 may be directly connected to the image registration server 92. In this way, a rate of data transmission between the image registration server 92 and the control server 10 is relatively high, and the control server 10 may control an image processing operation of the image registration server 92 more quickly. The image registration server 92 may also send the registration information of the first image to the control server 10 more quickly, such that the control server 10 may perform the position control operations in time. Furthermore, referring to FIG. 11, the control server 10 and the image registration server 92 may also be integrated in one physical machine to reduce the number of hardware to be deployed.

Further, referring to FIG. 12, FIG. 13, FIG. 14, or FIG. 15, the image guiding device may further include an image display 11, which is arranged separately from the gantry 1.

Figure 12:
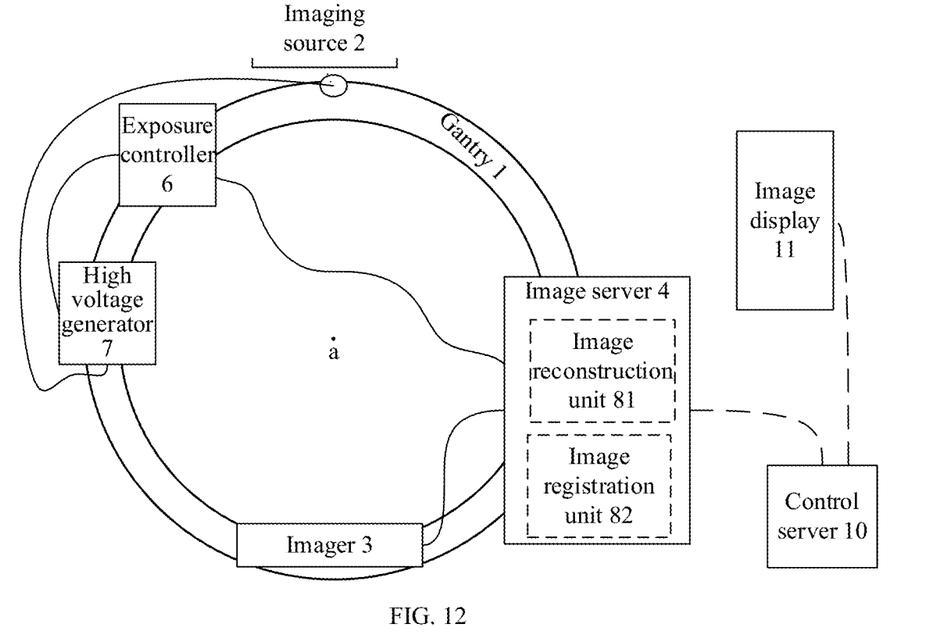
FIG. 12 is a schematic structural diagram of an eleventh image guiding device according to an embodiment of the present disclosure.
Figure 13:
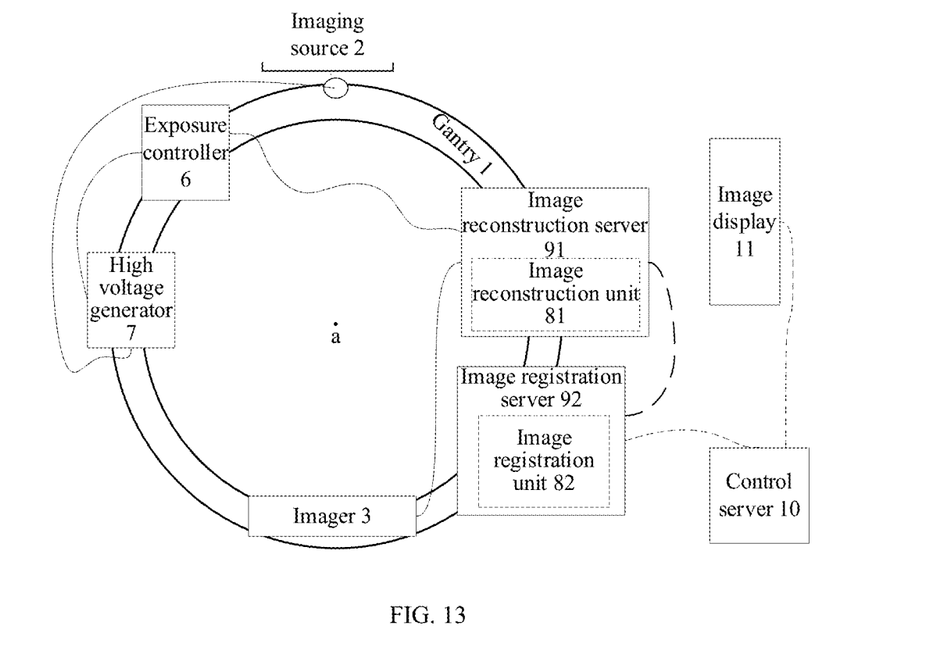
FIG. 13 is a schematic structural diagram of a twelfth image guiding device according to an embodiment of the present disclosure.
Figure 14:
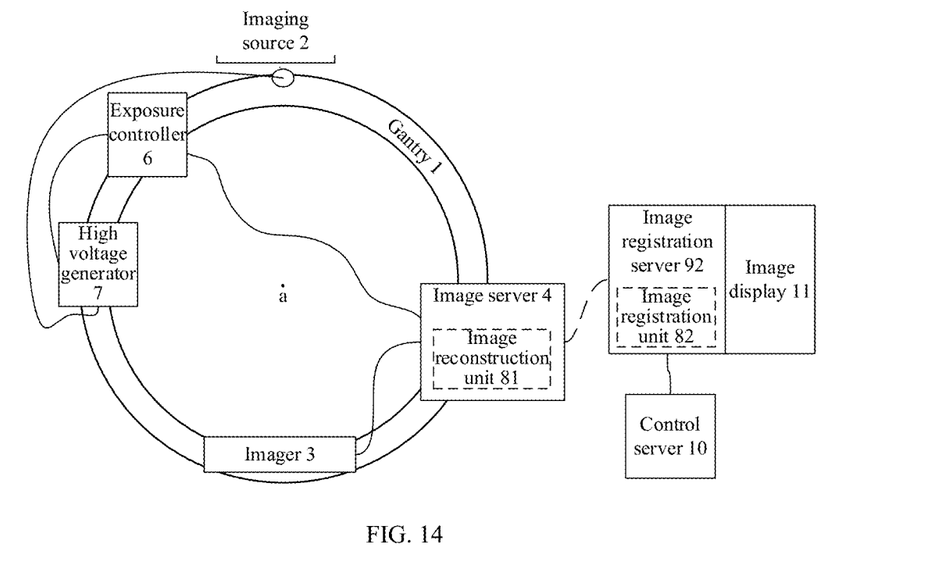
FIG. 14 is a schematic structural diagram of a thirteenth image guiding device according to an embodiment of the present disclosure.
Figure 15:
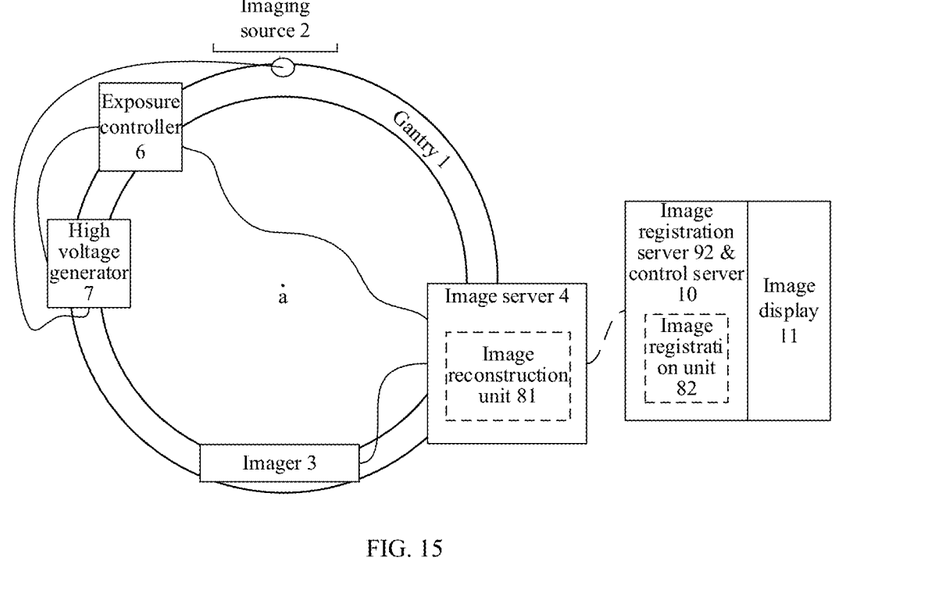
FIG. 15 is a schematic structural diagram of a fourteenth image guiding device according to an embodiment of the present disclosure.

Referring to FIG. 12 or FIG. 13, when the image server 4 includes an image reconstruction unit 81 and an image registration unit 82, or when the image server 4 includes an image reconstruction server 91 and an image registration server 92, the image display 11 is in communication with the control server 10. Referring to FIG. 14 or FIG. 15, when the image registration server 92 is arranged separately from the gantry 1, the image display 11 is in communication with the image registration server 92.

It should be noted that, when the image display 11 is in communication with the control server 10, or when the image display 11 is in communication with the image registration server 92, the communicative connection may be established over a wired network or a wireless network. For example, the image display 11 may be connected to the control server 10 by a display signal line such as video graphics array (VGA).

In addition, the image registration unit 82 may send the second image to the image display 11. The image display 11 may display the second image while receiving the second image. After the image display 11 displays the second image, a radiotherapist can review the second image so as to perform the subsequent radiotherapy accordingly.

It is worth noting that, when the image registration server 92 is arranged separately from the gantry 1, referring to FIG. 14 or FIG. 15, the image display 11 may be directly connected to the image registration server 92. In this way, a rate of data transmission between the image display 11 and the image registration server 92 is relatively high, and the image registration server 92 may send the second image to the image display 11 for display more quickly. In addition, user operation information in a display interface of the image display 11 may also be sent to the image registration server 92 more quickly, thereby effectively avoiding jams and improving user experience.

In the embodiment of the present disclosure, the image guiding device includes the gantry, the imaging source, the imager, and an image server. The imaging source, the imager, and the image server are all mounted on the gantry, and the imager is connected to the image server. When the gantry rotates, the imager and the image server are in a stationary state relative to each other. As the imager is directly connected to the image server, a rate of data transmission between the imager and the image server is relatively high, and the imager may send the projection data to the image server completely and accurately. In this way, the image of the affected part obtained by the image server according to the projection data is more accurate and the image quality is higher, thereby improving the subsequent positioning and image guiding effects. In addition, the cost can be greatly reduced since the slip ring arrangement is omitted from the image guiding device.

Another embodiment of the present disclosure provides a radiotherapy equipment. The radiotherapy equipment includes the image guiding device in the above embodiment.

It should be noted that, in practice, the radiotherapy equipment may not only include the above-mentioned image guiding device, but also include other components for implementing radiotherapy, which is not limited in the embodiment of the present disclosure.

In the embodiment of the present disclosure, the radiotherapy equipment includes the image guiding device. The image guiding device includes a gantry, an imaging source, an imager, and an image server. The imaging source, the imager and the image server are all mounted on the gantry, and the imager is connected to the image server. When the gantry rotates, the imager and the image server are in a stationary state relative to each other. As the imager is directly connected to the image server, a rate of data transmission between the imager and the image server is relatively high, and the imager may send the projection data to the image server completely and accurately. In this way, an image of an affected part obtained by the image server according to the projection data is more accurate and the image quality is higher, thereby improving the subsequent positioning and image guiding effects. In addition, the cost can be greatly reduced since the slip ring arrangement is omitted from the image guiding device.

Described above are merely optional embodiments of the present disclosure, and are not intended to limit the present disclosure. Within the spirit and principles of the present disclosure, any modifications, equivalent substitutions, improvements, and the like should fall within the protection scope of the present disclosure.

What is claimed is:

1. An image guiding device, comprising:
a gantry;
an imaging source mounted on the gantry, wherein the imaging source is configured to emit X-rays;
an imager arranged on the gantry in a fashion of facing the imaging source, wherein the imager is configured to receive the X-rays passing through an affected part of a patient and generate projection data according to the received X-rays; and
an image server mounted on the gantry and connected to the imager, wherein the image server is configured to receive the projection data and process the projection data to obtain an image of the affected part, and the image server comprises an image reconstruction unit;
an image registration server, wherein the image server is in communication with the image registration server over a wireless network, the image registration server is arranged separately from the gantry, and the image registration server comprises an image registration unit; and
a control server arranged separately from the gantry, wherein the control server is in communication with the image registration server;
wherein the image reconstruction unit is configured to reconstruct the projection data to obtain a first image, and send the first image to the image registration unit; the image registration unit is configured to register the first image to obtain registration information of the first image; and the control server is configured to receive the registration information of the first image and perform position control operations according to the registration information.

2. The image guiding device according to claim 1, wherein the image registration unit is configured to adjust the first image according to the registration information to obtain a second image.

3. The image guiding device according to claim 1, wherein the control server and the image registration server are integrated in one physical machine.

4. The image guiding device according to claim 2, further comprising an image display arranged separately from the gantry;
wherein the image display is in communication with the image registration server.

5. The image guiding device according to claim 1, further comprising an exposure controller and a high voltage generator; wherein
the exposure controller and the high voltage generator are mounted on the gantry, the exposure controller is respectively connected to the high voltage generator and the image server, and the high voltage generator is connected to the imaging source; and
wherein the image server is configured to send a scanning instruction message to the exposure controller; and the exposure controller is configured to control the imaging source to emit the X-rays by the high voltage generator and control the imager to receive the X-rays according to the scanning instruction message.

6. The image guiding device according to claim 1, further comprising a treatment couch; wherein
the treatment couch is mounted in an accommodation chamber of the gantry.

7. The image guiding device according to claim 1, wherein the gantry is rotatable around a rotation center thereof at any angle within 360 degrees.

8. The image guiding device according to claim 1, wherein the imaging source is an X-rays tube, and the imager is a flat panel detector.

9. Radiotherapeutic equipment, comprising an image guiding device and other components for implementing radiotherapy, wherein the image guiding device comprises:
a gantry;
an imaging source mounted on the gantry, wherein the imaging source is configured to emit X-rays;
an imager arranged on the gantry in a fashion of facing the imaging source, wherein the imager is configured to receive the X-rays passing through an affected part of a patient and generate projection data according to the received X-rays; and
an image server mounted on the gantry and connected to the imager, wherein the image server is configured to receive the projection data and process the projection data to obtain an image of the affected part, and the image server comprises an image reconstruction unit;
an image registration server, wherein the image server is in communication with the image registration server over a wireless network, the image registration server is arranged separately from the gantry, and the image registration server comprises an image registration unit; and
a control server arranged separately from the gantry, wherein the control server is in communication with the image registration server; wherein
the image reconstruction unit is configured to reconstruct the projection data to obtain a first image, and send the first image to the image registration unit; the image registration unit is configured to register the first image to obtain registration information of the first image; and the control server is configured to receive the registration information of the first image and perform position control operations according to the registration information.

10. The radiotherapeutic equipment according to claim 9, wherein the image registration unit is configured to adjust the first image according to the registration information to obtain a second image.

11. The radiotherapeutic equipment according to claim 9, wherein the control server and the image registration server are integrated in one physical machine.

12. The radiotherapeutic equipment according to claim 10, further comprising an image display arranged separately from the gantry; wherein
the image display is in communication with the image registration server.

13. The radiotherapeutic equipment according to claim 9, further comprising an exposure controller and a high voltage generator; wherein
the exposure controller and the high voltage generator are mounted on the gantry, the exposure controller is respectively connected to the high voltage generator and the image server, and the high voltage generator is connected to the imaging source; and
wherein the image server is configured to send a scanning instruction message to the exposure controller; and the exposure controller is configured to control the imaging source to emit the X-rays by the high voltage generator and control the imager to receive the X-rays according to the scanning instruction message.

14. The radiotherapeutic equipment according to claim 9, further comprising a treatment couch; wherein
the treatment couch is mounted in an accommodation chamber of the gantry.

15. The radiotherapeutic equipment according to claim 9, wherein the gantry is rotatable around a rotation center thereof at any angle within 360 degrees.

16. The radiotherapeutic equipment according to claim 9, wherein the imaging source is an X-rays tube, and the imager is a flat panel detector.

17. The image guiding device according to claim 2, wherein the gantry is rotatable around a rotation center thereof at any angle within 360 degrees.

18. The image guiding device according to claim 2, wherein the imaging source is a bulb tube, and the imager is a flat panel detector.

19. The radiotherapeutic equipment according to claim 16, wherein the other components comprises a device configured to provide a translational or rotational movement of the treatment couch.

* * * * *